(12) United States Patent
Sato

(10) Patent No.: US 12,728,178 B2
(45) Date of Patent: Sep. 8, 2026

(54) WORK TYPE IDENTIFICATION APPARATUS, CONTROL METHOD, AND NON-TRANSITORY COMPUTER READABLE MEDIUM

(71) Applicant: NEC Corporation, Tokyo (JP)

(72) Inventor: Shota Sato, Tokyo (JP)

(73) Assignee: NEC CORPORATION, Tokyo (JP)

( * ) Notice: Subject to any disclaimer, the term of this patent is extended or adjusted under 35 U.S.C. 154(b) by 390 days.

(21) Appl. No.: 18/275,994

(22) PCT Filed: Jan. 6, 2022

(86) PCT No.: PCT/JP2022/000264
§ 371 (c)(1),
(2) Date: Aug. 4, 2023

(87) PCT Pub. No.: WO2022/176424
PCT Pub. Date: Aug. 25, 2022

(65) Prior Publication Data

US 2024/0100210 A1 Mar. 28, 2024

(30) Foreign Application Priority Data

Feb. 16, 2021 (JP) ................................ 2021-022854

(51) Int. Cl.
*A61L 2/24* (2006.01)
*A61L 2/18* (2026.01)
(Continued)

(52) U.S. Cl.
CPC .................. *A61L 2/24* (2013.01); *A61L 2/18* (2013.01); *B08B 1/143* (2024.01); *B08B 3/08* (2013.01);
(Continued)

(58) Field of Classification Search
CPC .......... A61L 2/24; A61L 2/18; A61L 2202/14; A61L 2202/17; B08B 1/143; B08B 3/08; G06F 3/14
(Continued)

(56) References Cited

U.S. PATENT DOCUMENTS

2005/0216126 A1* 9/2005 Koselka ............ G08B 21/0423 901/2
2012/0066144 A1 3/2012 Berkvens et al.
(Continued)

FOREIGN PATENT DOCUMENTS

CN 109099359 A 12/2018
DE 102011105001 A1 8/2012
(Continued)

OTHER PUBLICATIONS

International Search Report for PCT Application No. PCT/JP2022/000264, mailed on Mar. 1, 2022.

*Primary Examiner* — Md Azad

(57) ABSTRACT

A work type identification apparatus (2000) acquires, for a target region (12) of a target object (10) on which a wiping work is to be performed, a 5 temperature data sequence (40) indicating a time variation of a temperature of the target region (12). The work type identification apparatus (2000) determines a type of wiping work performed on the target region (12) based on the time variation of the temperature of the target region (12) indicated by the temperature data sequence (40).

17 Claims, 6 Drawing Sheets

(51) Int. Cl.
*B08B 1/14* (2024.01)
*B08B 3/08* (2006.01)
*G06F 3/14* (2006.01)

(52) U.S. Cl.
CPC ............ *G06F 3/14* (2013.01); *A61L 2202/14* (2013.01); *A61L 2202/17* (2013.01)

(58) Field of Classification Search
USPC ............................................................ 700/28
See application file for complete search history.

(56) References Cited

U.S. PATENT DOCUMENTS

2018/0343859 A1* 12/2018 Jiang .................... C11D 17/049
2019/0365170 A1 12/2019 Möwisch
2020/0368901 A1* 11/2020 Takahashi ................ G06N 3/09
2022/0160918 A1* 5/2022 Beck ....................... G10L 25/66
2022/0366572 A1* 11/2022 Ding ....................... G06T 7/246

FOREIGN PATENT DOCUMENTS

JP 2012-528373 A 11/2012
WO 2017/170098 A1 10/2017

* cited by examiner

WORK TYPE IDENTIFICATION APPARATUS, CONTROL METHOD, AND NON-TRANSITORY COMPUTER READABLE MEDIUM

This application is a National Stage Entry of PCT/JP2022/000264 filed on Jan. 6, 2022, which claims priority from Japanese Patent Application 2021-022854 filed on Feb. 16, 2021, the contents of all of which are incorporated herein by reference, in their entirety.

TECHNICAL FIELD

The present disclosure relates to a technique for performing an analysis related to a work.

BACKGROUND ART

Disinfection and cleaning work is performed in various facilities. Systems have been developed to support such work. Patent Literature 1, for example, discloses a technique for detecting a presence of a place to be cleaned by detecting that a plate, cup, etc., are left on a table, or by detecting that a chair is not being used.

CITATION LIST

Patent Literature

Patent Literature 1: Published Japanese Translation of PCT International Publication for Patent Application, No. 2012-528373

SUMMARY OF INVENTION

Technical Problem

One of the disinfection and cleaning work involves wiping. However, Patent Literature 1 describes nothing about wiping work. The present disclosure has been made in view of this problem, and one of objects of the present disclosure is to provide a new technique for performing an analysis on a wiping work.

Solution to Problem

A work type identification apparatus according to the present disclosure includes: acquisition means for acquiring, for a target region of a target object on which a wiping work is to be performed, a temperature data sequence that indicates a time variation of a temperature of the target region; and identification means for determining a type of wiping work performed on the target region based on the time variation of the temperature of the target region indicated by the temperature data sequence.

A control method according to the present disclosure is executed by a computer. The control method includes: acquiring, for a target region of a target object on which a wiping work is to be performed, a temperature data sequence that indicates a time variation of a temperature of the target region; and determining a type of wiping work performed on the target region based on the time variation of the temperature of the target region indicated by the temperature data sequence.

A computer readable medium according to the present disclosure stores a program that causes a computer to execute the control method according to the present disclosure.

Advantageous Effects of Invention

According to the present disclosure, a new technique for performing an analysis on a wiping work is provided.

EXAMPLE EMBODIMENT

An example embodiment of the present disclosure is described in detail below with reference to the drawings. In each drawing, the same or corresponding elements are given the same symbols, and repeated descriptions are omitted as necessary for clarity. Unless otherwise explained, previously defined information such as predetermined values and thresholds is stored in advance in a storage device or the like accessible from an apparatus using the information.

Figure 1:
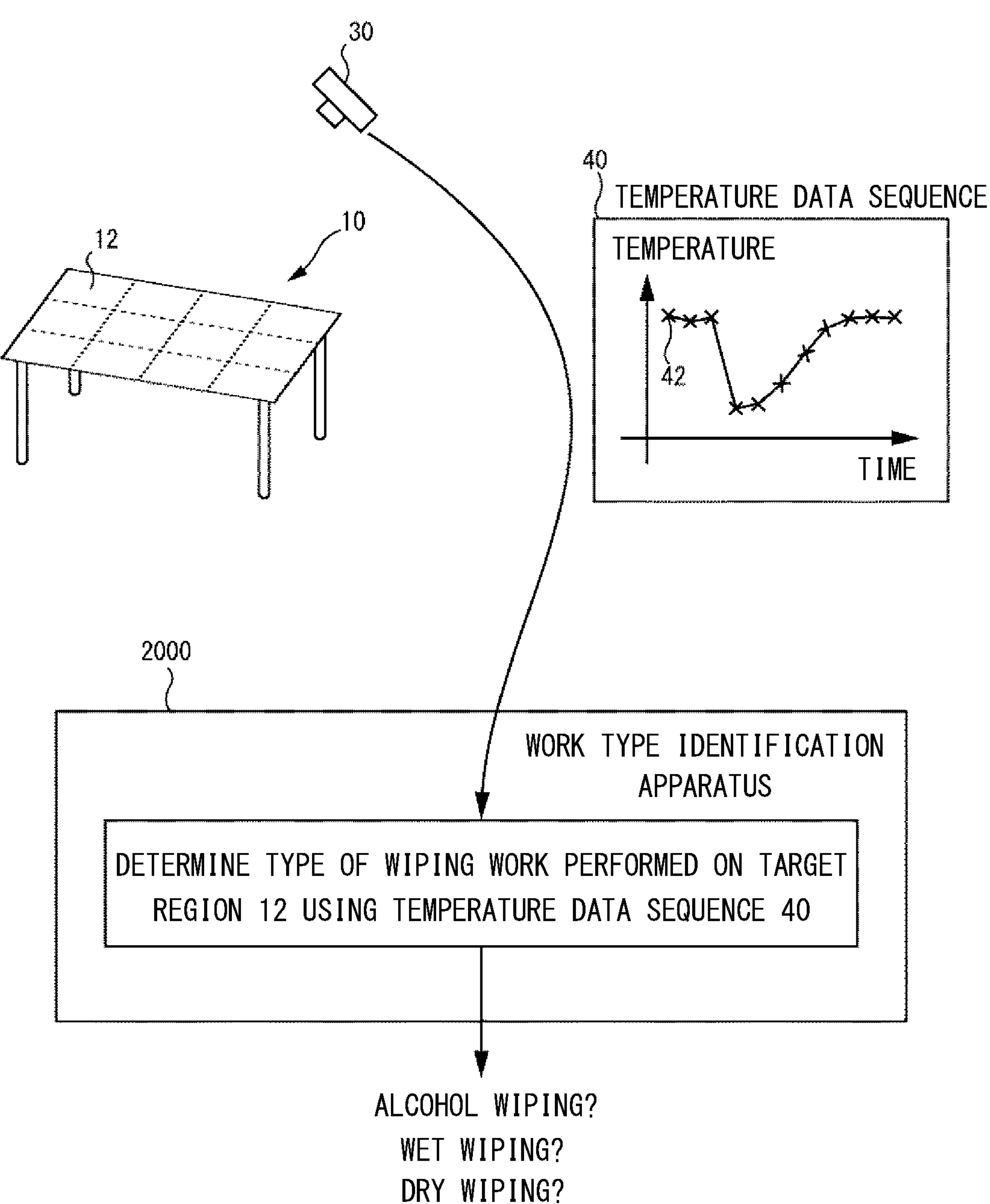
FIG. 1 shows an example of an overview of an operation of a work type identification apparatus according to a first example embodiment.

FIG. 1 shows an example of an overview of an operation of a work type identification apparatus 2000 according to a first example embodiment. Here, FIG. 1 is a diagram for facilitating the understanding of the overview of the work type identification apparatus 2000, and an operation of the work type identification apparatus 2000 is not limited to that shown in FIG. 1.

The work type identification apparatus 2000 determines a type of wiping work performed on a target region 12 of a target object 10. The target object 10 is any object subject to a wiping work, such as a wall, table, or floor. The target region 12 is a region on the surface of the target object 10. The target region 12 may be the entire region on the surface of the target object 10 or a partial region on the surface of the target object 10. In the latter case, for example, the surface of the target object 10 is divided into a plurality of regions according to a predetermined criterion, and each of the plurality of regions is handled as the target region 12. In the example of FIG. 1, a table is the target object 10, and a tabletop of the table is divided into twelve target regions 12.

A plurality of types of wiping work can be performed on the target region 12. The types of wiping work include alcohol wiping, wet wiping, and dry wiping. Alcohol wiping is a wiping work performed using alcohol. For example, alcohol wiping is a work in which a disinfectant containing alcohol is sprayed on the target region 12 and the target region 12 is wiped with a cloth or the like. Wet wiping is a wiping work performed using water. For example, wet wiping is a work in which water is sprayed on the target region 12 and the target region 12 is wiped with a cloth or the like, or the target region 12 is wiped with a cloth wet with water or the like. It should be noted that a wiping work using a disinfectant containing alcohol less than a standard amount may be classified as wet wiping rather than alcohol wiping. Dry wiping is a work of wiping the target region 12 with a dry cloth.

For example, the work type identification apparatus 2000 identifies which of the three types of wiping work described above has been performed on the target region 12. In addition, for example, any two of the three types of wiping work may be handled as wiping works that are possible to be performed on the target region 12. In this case, for example, the work type identification apparatus 2000 determines whether the wiping work performed on the target region 12 is alcohol wiping or wet wiping, or whether the wiping work performed on the target region 12 is wet wiping or dry wiping.

The work type identification apparatus 2000 identifies the type of wiping work performed on the target region 12 based on a time variation of a temperature of the target region 12. For example, it is considered that there is a difference between the time variation of the temperature of the target region 12 sprayed with alcohol and that of the target region 12 sprayed with water. Therefore, the type of wiping work is determined based on the difference in the time variation of the temperature of the target region 12.

In order to determine the type of wiping work, the work type identification apparatus 2000 acquires a temperature data sequence 40 indicating the time variation of the temperature of the target region 12. The temperature data sequence 40 is time series data that indicates temperature data 42 indicating a temperature of the target region 12 at a specific time point for each of a plurality of time points. The temperature data 42 is obtained by measuring the temperature of the target region 12 with a temperature sensor 30. For example, the temperature sensor 30 is a thermal camera that can obtain a distribution of temperatures on an object within a field of view. The thermal camera is implemented by, for example, an infrared camera.

For example, the temperature sensor 30 periodically repeats the measurement of the temperature of the target region 12. As a result, the temperature data 42 by which the temperature of the target region 12 can be determined is obtained for each of a plurality of time points. The temperature data 42 may indicate an absolute temperature at a specific time point or a difference from the last measured temperature. The temperature data sequence 40 shows a plurality of pieces of the temperature data 42 obtained in that way in time series.

The work type identification apparatus 2000 specifies a type of wiping work performed on the target region 12 based on the time variation of the temperature of the target region 12 indicated by the temperature data sequence 40. The specific method of specifying a type of wiping work will be described later.

<Example of Advantageous Effect>

According to the work type identification apparatus 2000 of this example embodiment, the temperature data sequence 40 indicating the time variation of the temperature of the target region 12 of the target object 10, which is subject to a wiping work, is acquired. The temperature data sequence 40 is then used to determine the type of wiping work performed on the target region 12. In this way, the type of wiping work performed on the target region 12 can be easily known.

Here, another way to know which type of wiping work has been performed is to check manually or receive a self-report of a worker. However, these methods require more time and effort to check and report. In addition, it is difficult to know when a mistake has occurred in the work, such as when a worker mistakenly performs wet wiping while being supposed to perform alcohol wiping. In this regard, according to the work type identification apparatus 2000, since the type of wiping work is automatically determined by a computer, no extra time and effort is required, unlike manual checking and reporting. . . . In addition, a wrong wiping work performed by the worker performs can be detected.

The work type identification apparatus 2000 according to this example embodiment will be described in more detail below.

<Example of Functional Configuration >

Figure 2:
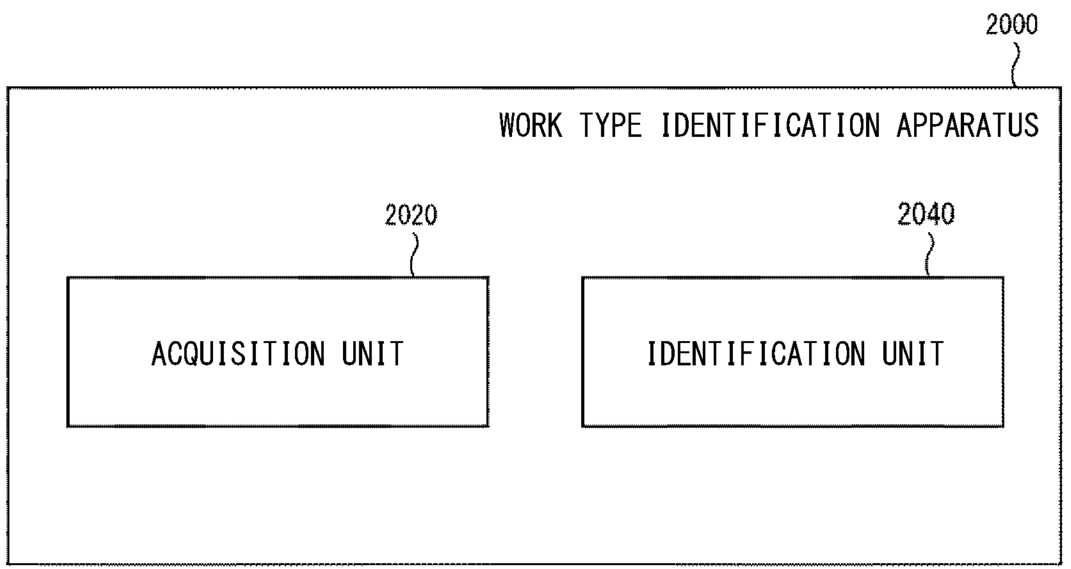
FIG. 2 is a block diagram showing an example of a functional configuration of the work type identification apparatus according to the first example embodiment.

FIG. 2 is a block diagram showing an example of a functional configuration of the work type identification apparatus 2000 according to the first example embodiment. The work type identification apparatus 2000 has an acquisition unit 2020 and an identification unit 2040. The acquisition unit 2020 acquires the temperature data sequence 40 indicating the time variation of the temperature of the target region 12 of the target object 10. The identification unit 2040 determines the type of wiping work performed on the target region 12 based on the time variation of the temperature of the target region 12 indicated by the temperature data sequence 40.

<Example of Hardware Configuration >

Each of the functional components of the work type identification apparatus 2000 may be implemented by hardware (e.g., hardwired electronic circuit, etc.) that implements each functional component, or by a combination of hardware and software (e.g., combination of an electronic circuit and a program that controls it, etc.). The case where each of the functional components of the work type identification apparatus 2000 is implemented by a combination of hardware and software will be further described below.

Figure 3:
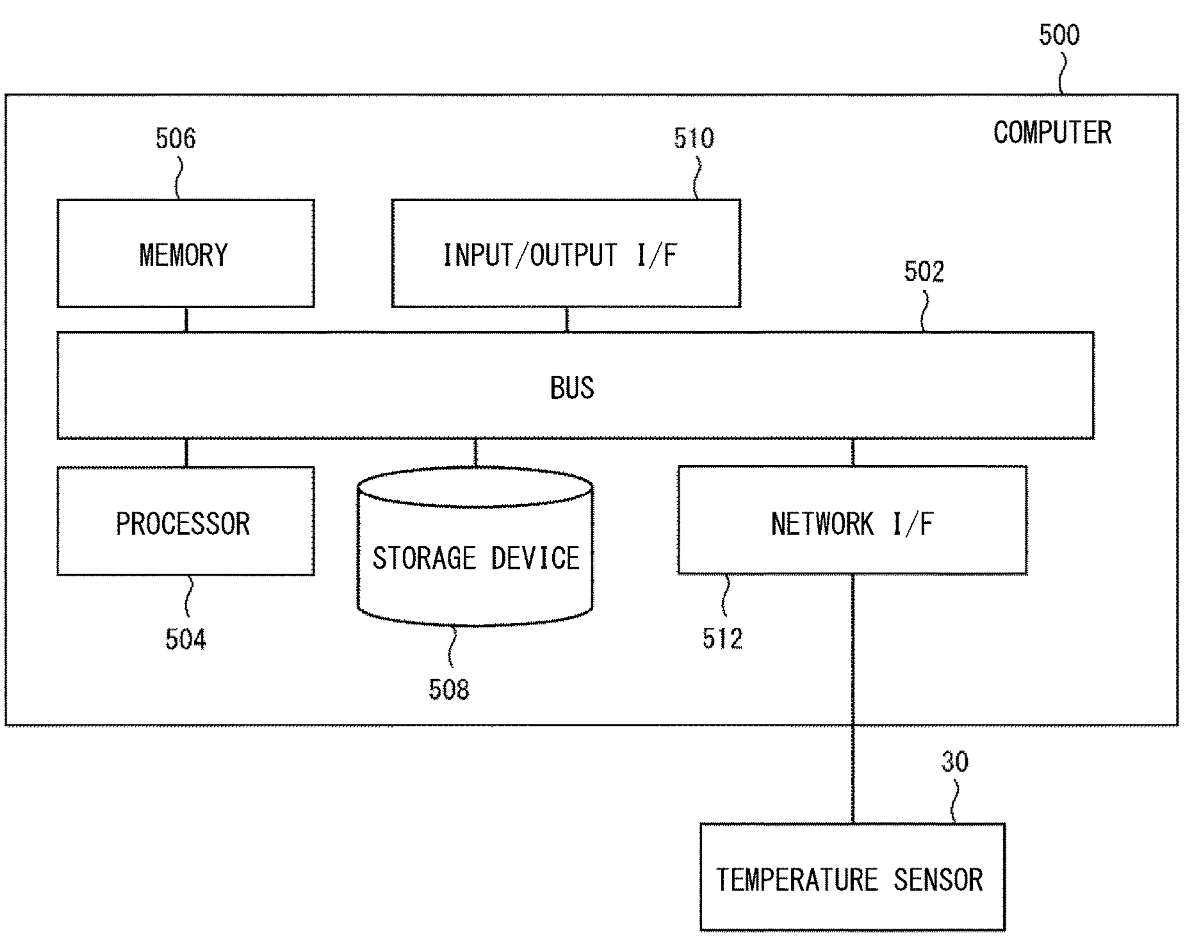
FIG. 3 is a block diagram showing an example of a hardware configuration of a computer implementing the work type identification apparatus.

FIG. 3 is a block diagram showing an example of a hardware configuration of a computer 500 for implementing the work type identification apparatus 2000. The computer 500 is any computer. For example, the computer 500 is a server machine or a stationary computer such as a PC (Personal Computer). Alternatively, for example, the computer 500 is a portable computer such as a smartphone or a tablet terminal. The computer 500 may be a special-purpose computer designed to implement the work type identification apparatus 2000 or a general-purpose computer.

For example, each function of the work type identification apparatus 2000 is implemented by the computer 500 installing a predetermined application thereto. The above application is composed of a program for implementing each functional component of the work type identification apparatus 2000. The method of acquiring the above program may be any method. For example, the program can be acquired from a storage medium (such as a DVD disc or USB memory) in which the program is stored. In addition, the program can be acquired, for example, by downloading the program from a server apparatus managing a storage apparatus in which the program is stored.

The computer 500 has a bus 502, a processor 504, a memory 506, a storage device 508, an input/output interface 510, and a network interface 512. The bus 502 is a data transmission path for the processor 504, the memory 506, the storage device 508, the input/output interface 510, and the network interface 512 to transmit and receive data to and from each other. However, the method of connecting the processors 504 and the like to each other is not limited to bus connection.

The processor 504 is one of various processors such as CPU (Central Processing Unit), GPU (Graphics Processing Unit), FPGA (Field-Programmable Gate Array), and DSP (Digital Signal Processor). The memory 506 is a primary storage device implemented using RAM (Random Access Memory) or the like. The storage device 508 is a secondary storage device implemented using a hard disk, SSD (Solid State Drive), memory card, ROM (Read Only Memory), or the like.

The input/output interface 510 is an interface for connecting the computer 500 to an input/output device. For example, an input apparatus such as a keyboard and an output device such as a display apparatus are connected to the input/output interface 510.

The network interface 512 is for connecting the computer 500 to a network. Note that this network may be a Local Area Network (LAN) or a Wide Area Network (WAN). For example, the computer 500 is communicatively connected to the temperature sensor 30 via the network. However, the computer 500 need only be able to somehow acquire the temperature data sequence 40 generated by the temperature sensor 30, and need not be communicatively connected to the temperature sensor 30.

The storage device 508 stores programs (programs for implementing the applications described above) for implementing respective functions of the work type identification apparatus 2000. The processor 504 reads these programs into the memory 506 and executes them to implement the respective functions of the work type identification apparatus 2000.

The work type identification apparatus 2000 may be implemented by one computer 500 or by a plurality of the computers 500. In the latter case, the configuration of each computer 500 need not be identical and instead may be different from each other.

<Flow of Processing>

Figure 4:
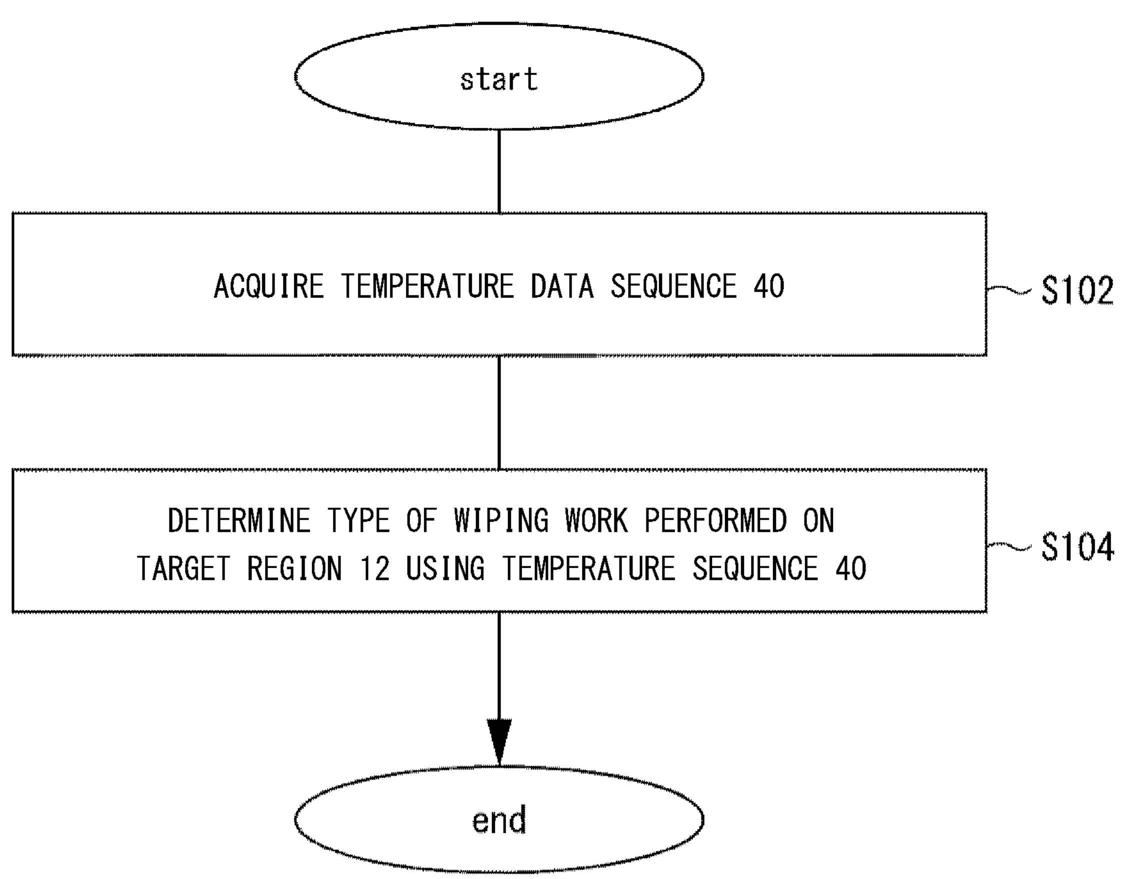
FIG. 4 is a flowchart showing an example of a flow of processing executed by the work type identification apparatus according to the first example embodiment.

FIG. 4 is a flowchart showing an example of a flow of processing executed by the work type identification apparatus 2000 according to the first example embodiment. The acquisition unit 2020 acquires the temperature data sequence 40 (S102). The identification unit 2040 uses the temperature data sequence 40 to determine the type of wiping work performed on the target region 12 (S104).

<As to Temperature Data Sequence 40>

As mentioned above, the temperature data sequence 40 is time series data of the temperature data 42. The temperature data 42 shows the temperature of the target region 12 at a specific time point. The temperature data 42 is generated by the temperature sensor 30.

Here, the temperature sensor 30 may measure the temperature for each of a plurality of regions. For example, a thermal camera generates a thermal image showing a temperature distribution of an object included in its angle of view. Each pixel in the thermal image indicates a temperature of the region on the object corresponding to that pixel.

Here, one target region 12 may span a plurality of pixels in the thermal image. In this case, the temperature of the target region 12 is determined using the temperature indicated by any one or more of the plurality of pixels corresponding to that target region 12. For example, the temperature of the target region 12 is determined as a statistic (mean, median, mode, minimum, or maximum, etc.) of the temperatures indicated by a plurality of pixels corresponding to that target region 12. In another example, one pixel to be used as indicating the temperature of the target region 12 (hereinafter, referred to as a representative pixel) is defined in advance among a plurality of pixels corresponding to the target region 12. In this case, the temperature indicated by the representative pixel corresponding to the target region 12 is handled as the temperature of the target region 12. The association between the pixels on the thermal image and the target region 12 is defined in advance.

<Acquisition of Temperature Data Sequence 40: S102>

The acquisition unit 2020 acquires the temperature data sequence 40 (S102). There are various methods for the acquisition unit 2020 to acquire the temperature data sequence 40. For example, the temperature sensor 30 measures the temperature, generates the temperature data 42, and then puts the temperature data 42 in a storage unit. In this case, the acquisition unit 2020 acquires the temperature data 42 newly stored in the storage unit by repeatedly accessing the storage unit. By acquiring a plurality of pieces of the temperature data 42 generated by the temperature sensor 30 in this way, the temperature data sequence 40 can be acquired. However, the acquisition unit 2020 may acquire the temperature data sequence 40 in one access by collectively acquiring the plurality of pieces of the temperature data 42 stored in the storage unit.

In addition, for example, the temperature sensor 30 may be configured to transmit the temperature data 42 to the work type identification apparatus 2000.

In this case, the acquisition unit 2020 can obtain the temperature data sequence 40 composed of the acquired plurality of pieces of the temperature data 42. It is noted that the temperature sensor 30 may transmit the temperature data sequence 40 to the work type identification apparatus 2000 at the same time by transmitting the plurality of pieces of the temperature data 42 collectively to the work type identification apparatus 2000.

Here, when the temperature sensor 30 is a thermal camera or the like as described above, the temperature can be measured for each of the plurality of regions. In this case, for example, the acquisition unit 2020 extracts data indicating the temperature of the target region 12 from the data generated by the temperature sensor 30. For example, when a thermal image is generated by the thermal camera as described above, the acquisition unit 2020 acquires the temperature data 42 by using pixels corresponding to the target region 12 in the pixels shown in the thermal image. For example, when the target region 12 corresponds to one pixel of the thermal image, the acquisition unit 2020 acquires a value of the temperature indicated by the pixel as the temperature data 42. Moreover, for example, when the target region 12 spans a plurality of pixels of the thermal image, the acquisition unit 2020 acquires a statistical value of the temperatures indicated by the plurality of pixels or a value of the temperature indicated by the representative pixel as the temperature data 42, as described above.

When there is a plurality of regions to be handled as the target regions 12 (when the type of wiping work is determined for each of the plurality of target regions 12), the acquisition unit 2020 acquires the temperature data 42 for each target region 12 by extracting the pixels of the thermal image corresponding to the target region 12, for each target region 12. However, it is not necessary a single temperature sensor 30 that measures the temperature of all the regions to be handled as the target regions 12, but a plurality of the temperature sensors 30 may be used instead.

<Determining Type of Wiping Work: S104 >

The identification unit 2040 uses the temperature data sequence 40 to determine the type of wiping work performed on the target region 12 (S104). For example, the identification unit 2040 extracts a plurality of partial data sequences of a predetermined length from the temperature data sequence 40, and for each partial data sequence, determines the type of wiping work performed on the target region 12 at the time corresponding to the partial data sequence. The adjacent partial data sequences may partially overlap each other.

Figure 5:
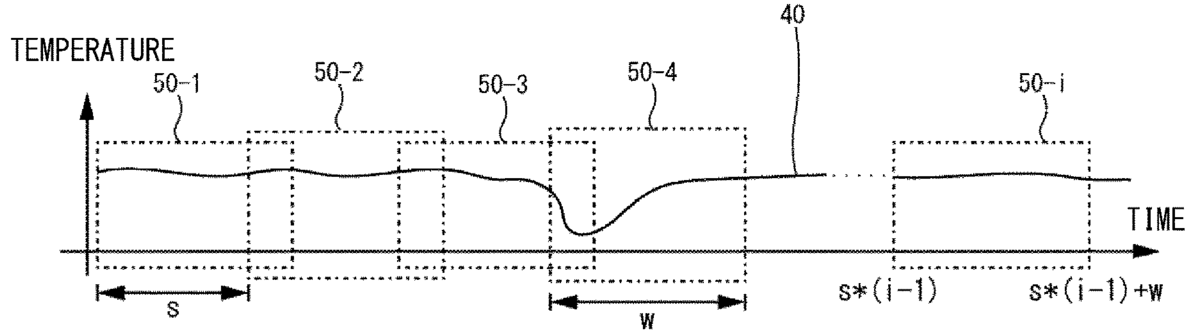
FIG. 5 shows an example of a relationship between a temperature data sequence and partial data sequences.

FIG. 5 shows an example of a relationship between the temperature data sequence 40 and partial data sequences 50. In FIG. 5, the partial data sequences 50 indicate temperature variations within w seconds. Also, each of starting positions of extraction of the partial data sequences 50 is slid by a width of s seconds. That is, the i-th partial data sequence 50 is time-series data composed of temperature data 42 from a time point $s*(i-1)$ to a time point $s*(i-1)+w$ among the temperature data 42 included in the temperature data sequence 40. It is note that the time point referred to here is a relative time point where the time point of the measurement of the first temperature data 42 included in the temperature data sequence 40 is handled as being 0.

However, the identification unit 2040 may determine the type of wiping work performed during a period of time indicated by a whole of the temperature data sequence 40, without extracting the partial data sequence 50 from the temperature data sequence 40. For example, it may be configured to detect that a wiping work has been performed on the target region 12, and the temperature data sequence 40 for a period of time of a predetermined length (e.g., w in FIG. 5) from the starting point of the wiping work or a point close to it is acquired by the acquisition unit 2020. In this case, the whole of the temperature data sequence 40 is time-series data of the same length as that of the partial data sequence 50 in FIG. 5. A wiping work that has been performed on the target region 12 can be detected using, for example, video data obtained from a video camera that captures the target region 12.

Some specific examples of a method of determining the type of wiping work are described below. For the sake of simplicity, a case in which the type of wiping work is determined using the partial data sequence 50 is described. In a case of determining the type of wiping work performed during the period of time indicated by the whole of the temperature data sequence 40, the temperature data sequence 40 is used instead of the partial data sequence 50.

<<Method 1: Comparison of Feature Values>>

In this method, for each type of wiping works, a feature value of time-series data of the temperature of the region for which the wiping work of that type has been performed is predetermined. That is, the association between "a type of wiping work and a feature value of time-series data of the temperature of the wiped region" is created in advance. For example, in the case of alcohol wiping and wet wiping, it is assumed that the temperature decreases at the beginning of wiping and then increases thereafter. On the other hand, in dry wiping, the temperature is unlikely to change much. In addition, since alcohol evaporates faster than water, it is considered that the temperature variation in the case of alcohol wiping is faster than that in the case of wet wiping. In other words, it is considered that the alcohol-wiped region returns to a normal temperature faster than the water-wiped region. Thus, it is considered that the characteristics of the time variation in the temperature of the wiped region varies depending on the type of wiping work. Therefore, the feature value of the time-series data of temperature can be determined for each type of wiping work.

The identification unit 2040 extracts the feature value from the partial data sequence 50, and then computes the similarity between the extracted feature value and the predetermined feature value for each type of wiping work. Next, the identification unit 2040 determines the type of wiping work corresponding to the feature value having the highest similarity to the feature value extracted from the partial data sequence 50 as the type of wiping work performed on the target region 12.

If the highest similarity among the computed similarities is less than or equal to a threshold (i.e., when the feature value corresponding to any type of wiping work has low similarity to the feature value obtained from the partial data sequence 50), the identification unit 2040 may determine that no wiping work has been performed. For example, if the temperature sensor 30 is used to constantly measure the temperature of the target region 12, temperature data for a period of time during which no wiping work has been performed can also be included in the temperature data sequence 40. Therefore, by determining the type of wiping work for the plurality of partial data sequences 50 obtained from the temperature data sequence 40, the identification unit 2040 can determines two things for each partial data sequence 50, which are: 1) whether or not the partial data sequence 50corresponds to the period of time during which the wiping work has been performed, and 2) the type of wiping work that has been performed if the partial data sequence 50 corresponds to the period of time during which the wiping work has been performed.

The feature value of the time-series data of the temperature of the wiped region may be defined for each type of target object 10. For example, the feature value may be determined for each type of target object 10 such as a table, chair, floor, and wall. In addition, for example, the feature value may be defined for each material of the target object 10 such as wood or concrete. When the feature value is defined for each type of target object 10, the association between "a type of target object, a type of wiping work, and a feature value of time-series data of a temperature of a wiped region" is defined in advance. Further, when the feature value is defined for each material of the target object 10, the association between "a material of a target object, the a of wiping work, and a feature value of time-series data of a temperature of a wiped region" is defined in advance. The identification unit 2040 determines the type or material (hereinafter referred to as the type or the like) of the target object 10, and uses the feature value associated with the determined type or material.

The type or the like of the target object 10 may be determined by a user of the work type identification apparatus 2000 or may be automatically determined by the work type identification apparatus 2000. In the latter case, for example, the work type identification apparatus 2000 determines the type or the like of the target object 10 by analyzing an image obtained by capturing the target object 10 using a video camera (still camera or video camera). It is noted that it is possible to employ a well-known technique for a technique of identifying the type or the like of the object included in an image by using the image. Further, the processing to determine the type or the like of the target object 10 may be performed by a computer other than the work type identification apparatus 2000. In this case, the work type identification apparatus 2000 acquires information indicating the type or the like of the target object 10 from this computer.

When a plurality of target regions 12 are set for one object, the type, material or the like may differ for each target region 12. For example, when the target object 10 is a table, the types of target regions 12 include a tabletop or a support post. Therefore, the type or the like may be determined for each target region 12 instead of for each target object 10.

<<Method 2: Use of Identification Model>>

This method uses a trained identification model (hereinafter referred to as a work type identification model). The work type identification model is trained in advance to output a label indicating a type of wiping work in response to an input of time-series data of a temperature. Any type of model capable of handling time-series data, such as RNN (Recurrent Neural Network), can be used as the work type identification model.

Training of the work type identification model is carried out by using a plurality of pieces of training data, each of which has time-series data of a temperature of a region as input data and a label indicating a type of wiping work as a ground-truth label. It is noted that the work type identification model may be trained to be capable of identify that no wiping work has been performed by also using training data such as "input data: time-series data of temperatures in regions where no wiping work is performed, ground-truth label: no wiping work".

The identification unit 2040 acquires a label indicating the type of wiping work from the work type identification model by inputting the temperature data sequence 40 to the work type identification model. Next, the identification unit 2040 determines the type of wiping work indicated by the acquired label as the type of wiping work performed on the target region 12. When a label indicating that no wiping work has been performed is output, the identification unit 2040 determines that no wiping work has been performed on the target region 12.

In a manner similar to the case in which a feature value is used, the type or the like of the target object 10 or the target region 12 may be taken into consideration in the case in which the work type identification model is used. For example, a work type identification model is prepared for each type or the like of the target object 10 or the target region 12. In this case, training data is prepared for each type or the like of the target object 10 or the target region 12, and each work type identification model is trained. The identification unit 2040 determines the work type identification model corresponding to the type or the like of the target object 10 or the target region 12, whose temperature variation is indicated by the partial data sequence 50, and inputs the partial data sequence 50 to the work type identification model.

In addition, for example, data indicating the type or the like of the target object 10 or the target region 12 may be included in the input data of the work type identification model. In this case, data indicating the type or the like of the target object 10 or the target region 12 may also be included in the input data during training, so that the work type identification model is trained so as to identify the type of wiping work taking the type or the like of the target object 10 into consideration.

<Example of Usage Scene of Work Type Identification Apparatus 2000>

Hereinafter, a specific example of a usage scene of the work type identification apparatus 2000 is described in order to facilitate the understanding of the work type identification apparatus 2000. The following description is only an example of a usage scene, and a usage scene of the work type identification apparatus 2000 is not limited to the example described below.

For example, the work type identification apparatus 2000 is used to monitor whether or not alcohol wiping is performed on a table in a restaurant, food court, or other shops where food and drink are served. Therefore, each table is handled as a target object 10. The table is also divided into plurality of regions, and each region is handled as a target region 12. For each table, the type of wiping work is determined for all target regions 12 included in the table. For each table, it is determined that alcohol wiping has been performed if it is determined that the type of wiping work performed is alcohol wiping for all target regions 12 included in the table. It should be noted that not only tables but also chairs, floors, or the like may be further handled as objects to be subjected to a wiping work.

Figure 6:
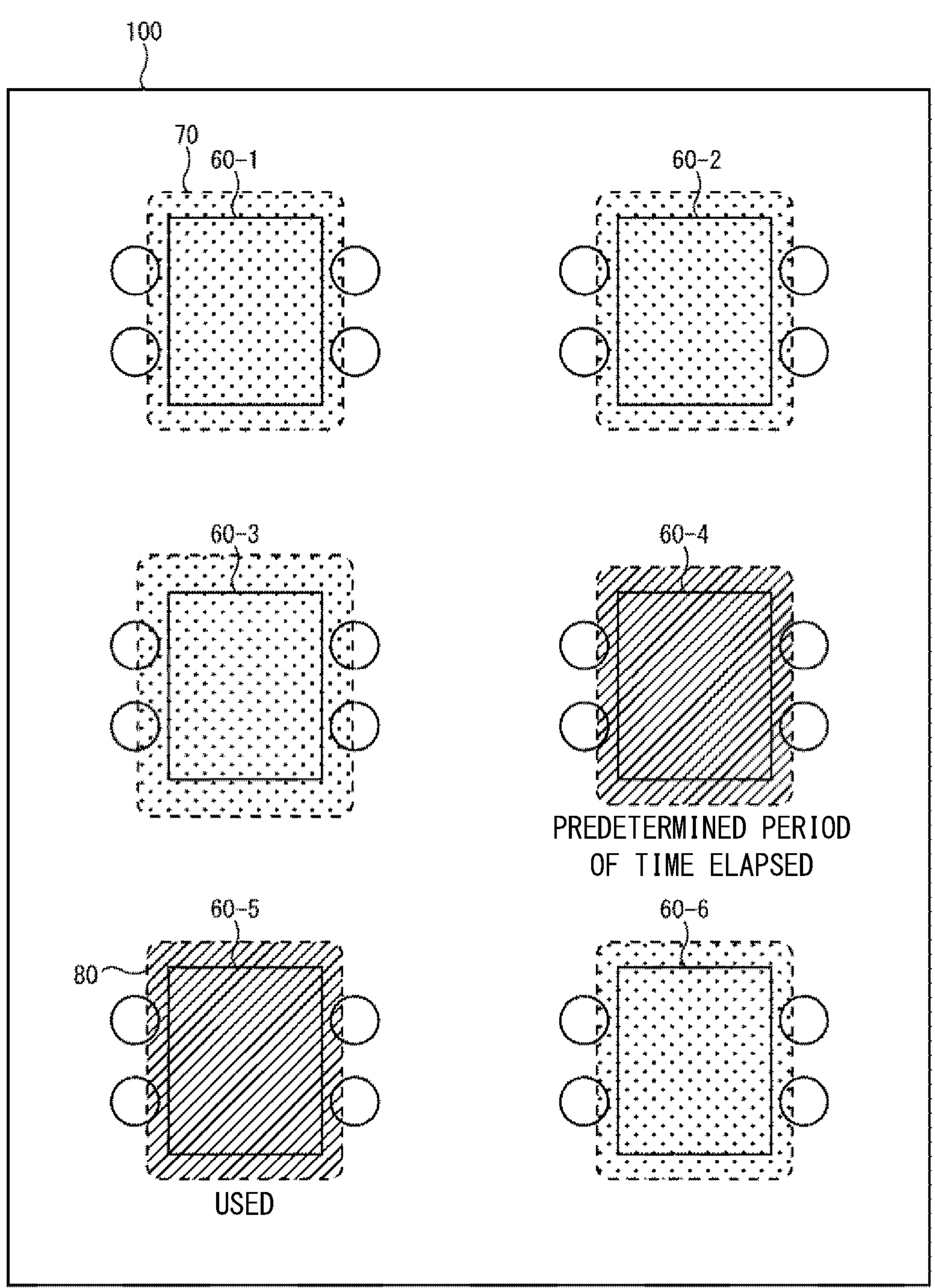
FIG. 6 shows an example of a screen output by the work type identification apparatus.

FIG. 6 shows an example of a screen output by the work type identification apparatus 2000. The screen in FIG. 6 is referred to as a browsing screen 100. In the work type identification apparatus 2000, a functional component unit that outputs the browsing screen 100 or outputs a notification, which will be described later, is referred to as an output unit (not illustrated). For each table 60, the browsing screen 100 shows a display indicating whether or not alcohol wiping should be performed (hereinafter this display referred to as a state display). A dot-patterned state display 70 shows a state in which alcohol wiping is not necessary (a state in which alcohol wiping has already been performed). On the other hand, a diagonal-patterned state display 80 shows a state in which alcohol wiping is necessary. Either the state display 70 or the state display 80 may not be displayed.

Here, the image of the table 60 or the like displayed on the browsing screen 100 may be an image obtained by capturing an actual shop or an image simulating the shop such as a floor plan of the shop. In the former case, images obtained from video cameras capturing the shop in real time may be used, or images of the shop captured by video cameras in the past may be used.

For example, the work type identification apparatus 2000 sets the states of all tables 60 to a state in which alcohol wiping is necessary before opening the store. Therefore, the state display 80 is displayed for all tables 60.

After that, the work type identification apparatus 2000 repeats the determination of whether or not alcohol wiping has been performed for each table 60 while the shop is open. Specifically, the work type identification apparatus 2000 determines that alcohol wiping has been performed on the table 60 when it is determined that alcohol wiping has been performed for all the target regions 12 included in the table 60. Next, the work type identification apparatus 2000 displays the state display 70 indicating that alcohol wiping is not necessary so as to be superimposed on the table 60. The work type identification apparatus 2000 also records the time when alcohol wiping is performed for each table 60.

Assume that the type of wiping work is determined to be alcohol wiping for not all but some of the twelve target regions 12 included in the table 60.

This is considered to be a situation where alcohol wiping is not performed for some of the tables 60. In such a situation, a clerk in charge of wiping the table 60 is likely to mistakenly think that alcohol wiping has been completed correctly. Therefore, it is preferable to enable the clerk to know that alcohol wiping has not been performed correctly.

Thus, for example, the work type identification apparatus 2000 may change the state display for such tables 60 to a display that a wiping work has been performed incompletely. In this way, it enables the clerk to know not only whether or not alcohol wiping is necessary for each table 60 but also that a wiping work has been performed incompletely by himself/herself or another clerk. The situation in which a wiping work has been performed incompletely may include not only a situation in which alcohol wiping has been performed only for some of the target regions 12 included in the table 60 as described above, but also a situation in which dry wiping or wet wiping has been performed on the entire table 60.

Furthermore, while the shop is open, the work type identification apparatus 2000 repeatedly determines whether or not a predetermined reset condition has been satisfied for each table 60. The reset condition is a condition that is satisfied when the state of the table 60 is a state in which alcohol wiping is necessary. For the table 60 for which the reset condition is satisfied, the work type identification apparatus 2000 changes the display to the state display 80.

For example, the reset condition is a condition that "table 60 has been used". This is because if the table 60 is used by a customer or the like, alcohol wiping must be performed on the table 60 before the next customer uses the table 60. For example, in the example of FIG. 6, a table 60-5 is superimposed with the state display 80, because this reset condition is satisfied. In addition, a label of "used" indicating that the reset condition is applied is displayed.

It is possible to detect that the table 60 has been used, for example, by analyzing videos of a video camera installed to monitor the inside of the shop. For example, a situation in which 1) an object has been placed on the table 60, 2) a person has sat on a chair installed in combination with the table 60, or 3) the table 60 or a chair has been moved is handled as a situation in which the table 60 has been used.

Another reset condition, for example, is that a predetermined period of time has elapsed since the last time alcohol wiping is performed on the table 60. By using such a reset condition, alcohol wiping can be performed periodically on the table 60. For example, in the example of FIG. 6, the state display 80 is superimposed on the table 60-4 when this reset condition is satisfied. In addition, a label of "predetermined period of time elapsed" is displayed to indicate that the reset condition is applied. The time of the last alcohol wiping is recorded by the work type identification apparatus 2000 as described above.

Here, a plurality of reset conditions may be used. In this case, the state display of the table 60 may be changed if any one of the plurality of reset conditions is satisfied, or the state display of the table 60 may be changed only if all reset conditions are satisfied for the table 60.

The browsing screen 100 can be displayed on any display apparatus. For example, in a shop, a display apparatus that displays the browsing screen 100 is provided at a position where the customer or the clerk can browse. By doing so, the customer can easily know the table where the alcohol wiping is done correctly, so that the customer can use the shop with a sense of security. In addition, the clerk who does the wiping work in the shop can easily know the table where the alcohol wiping should be done by browsing the display apparatus.

Furthermore, for example, the browsing screen 100 may be provided as a screen of an application or a website available on a mobile terminal. In this case, the customer or the clerk can browse the browsing screen 100 on a mobile terminal or the like used by the customer or the clerk.

In addition, if there is a table 60 in a state that requires alcohol wiping, the work type identification apparatus 2000 may transmit a notification that enables the clerk to know this table 60 to the clerk's mobile terminal, cash register terminal, or PC provided in backyard of the shop or the like. In this way, the clerk can easily know that there is a table 60 that should be alcohol wiped and which table 60 should be alcohol wiped.

The browsing screen 100 may show a display that enables the clerk to know the target region 12 where it is determined that no wiping work has been performed or the target region 12 where it is determined that a wiping work other than alcohol wiping has been performed. For example, instead of displaying the state display 80 to cover the entire table 60 as in the example of FIG. 6, the work type identification apparatus 2000 causes the state display 80 to be displayed so that it is superimposed only on the target region 12 for which it is determined that no wiping work has been performed.

Additionally, the browsing screen 100 may show a display using the temperature data sequence 40 together with the state display 70 or the state display 80, or in place of the state display 70 or the state display 80. For example, when a thermal camera is used as the temperature sensor 30, a thermal image generated by the thermal camera is displayed on the browsing screen 100. For example, when one thermal camera is used for each table 60, a thermal image obtained from the thermal camera is superimposed on the table 60 corresponding to the thermal camera and displayed. By showing such a display, a state of a temperature of each table 60 can be visually recognized by browsing the browsing screen 100.

Although the present disclosure has been described above with reference to the above example embodiment, the present disclosure is not limited to the above example embodiment. Various modifications can be made to the configurations and details of the present disclosure within the scope of the present disclosure that would be understood by those skilled in the art.

In the above example, the program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

The whole or part of the example embodiment disclosed above can be described as, but not limited to, the following supplementary notes.

(Supplementary Note 1)

A work type identification apparatus comprising:

acquisition means for acquiring, for a target region of a target object on which a wiping work is to be performed, a temperature data sequence that indicates a time variation of a temperature of the target region; and identification means for determining a type of wiping work performed on the target region based on the time variation of the temperature of the target region indicated by the temperature data sequence.

(Supplementary Note 2)

The work type identification apparatus according to Supplementary note 1, wherein the type of wiping work includes at least two of a wiping work performed using alcohol, a wet wiping, and a dry wiping.

(Supplementary Note 3)

The work type identification apparatus according to Supplementary note 1or 2, wherein for each type of wiping work, a feature value of time-series data indicating a time variation of a temperature of a region on which the wiping work of that type is stored in advance in a storage unit, and wherein the identification means extracts a feature value from time-series data included in the acquired temperature data sequence, and determines the type of wiping work performed on the target region based on a degree of similarity between the extracted feature value and the feature value stored in the storage unit for each type of wiping work.

(Supplementary Note 4)

The work type identification apparatus according to Supplementary note 3, wherein the feature value stored in the storage unit is defined for each type or material of the target object or the target region.

(Supplementary Note 5)

The work type identification apparatus according to Supplementary note 1or 2, wherein the identification means includes a model that has been trained to output, in response to an input of data indicating a time variation of a temperature of a region of an object, data indicating the type of wiping work performed on that region, and wherein the identification means determines the type of wiping work performed on the target region by inputting time-series data included in the acquired temperature data sequence to the model.

(Supplementary Note 6)

The work type identification apparatus according to Supplementary note 5, wherein the model is provided for each type or material of the target object or the target region, or wherein the data input to the model includes data indicating the type or material of the target object or the target region.

(Supplementary Note 7)

The work type identification apparatus according to any one of Supplementary notes 1 to 6, wherein the acquisition means acquires the temperature data sequence for each of a plurality of the target objects, wherein the identification means determines, for each of the plurality of target objects, the type of wiping work performed on the target region of the target object, and wherein the work type identification apparatus further comprises output means for outputting, together with an image representing the target object, a display enabling a user to know whether or not a specific type of wiping work has been performed on each of the target objects.

(Supplementary Note 8)

A control method executed by a computer comprising:

acquiring, for a target region of a target object on which a wiping work is to be performed, a temperature data sequence that indicates a time variation of a temperature of the target region; and determining a type of wiping work performed on the target region based on the time variation of the temperature of the target region indicated by the temperature data sequence.

(Supplementary Note 9)

The control method according to Supplementary note 8, wherein the type of wiping work includes at least two of a wiping work performed using alcohol, a wet wiping, and a dry wiping.

(Supplementary Note 10)

The control method according to Supplementary note 8 or 9, wherein for each type of wiping work, a feature value of time-series data indicating a time variation of a temperature of a region on which the wiping work of that type is stored in advance in a storage unit, and wherein in the identification of the type of wiping work, a feature value is extracted from time-series data included in the acquired temperature data sequence, and the type of wiping work performed on the target region is determined based on a degree of similarity between the extracted feature value and the feature value stored in the storage unit for each type of wiping work.

(Supplementary Note 11)

The work type identification apparatus according to Supplementary note 10, wherein the feature value stored in the storage unit is defined for each type or material of the target object or the target region.

(Supplementary Note 12)

The control method according to Supplementary note 8 or 9, wherein the computer includes a model that has been trained to output, in response to an input of data indicating a time variation of a temperature of a region of an object, data indicating the type of wiping work performed on that region, and wherein in the identification of the type of wiping work, the type of wiping work performed on the target region is determined by inputting time-series data included in the acquired temperature data sequence to the model.

(Supplementary Note 13)

The control method according to Supplementary note 12, wherein the model is provided for each type or material of the target object or the target region, or wherein the data input to the model includes data indicating the type or material of the target object or the target region.

(Supplementary Note 14)

The control method according to any one of Supplementary notes 8 to 13, wherein in the acquisition of the temperature data sequence, the temperature data sequence is acquired for each of a plurality of the target objects, wherein in the identification of the type of wiping work, for each of the plurality of target objects, the type of wiping work performed on the target region of the target object is determined, and wherein the control method further comprises outputting, together with an image representing the target object, a display enabling a user to know whether or not a specific type of wiping work has been performed on each of the target objects.

(Supplementary Note 15)

A non-transitory computer readable medium storing a program that causes a computer to execute:

acquiring, for a target region of a target object on which a wiping work is to be performed, a temperature data sequence that indicates a time variation of a temperature of the target region; and determining a type of wiping work performed on the target region based on the time variation of the temperature of the target region indicated by the temperature data sequence.

(Supplementary Note 16)

The computer readable medium according to Supplementary note 15, wherein the type of wiping work includes at least two of a wiping work performed using alcohol, a wet wiping, and a dry wiping.

(Supplementary Note 17)

The computer readable medium according to Supplementary note 15 or 16, wherein for each type of wiping work, a feature value of time-series data indicating a time variation of a temperature of a region on which the wiping work of that type is stored in advance in a storage unit, and wherein in the identification of the type of wiping work, a feature value is extracted from time-series data included in the acquired temperature data sequence, and the type of wiping work performed on the target region is determined based on a degree of similarity between the extracted feature value and the feature value stored in the storage unit for each type of wiping work.

(Supplementary Note 18)

The computer readable medium according to Supplementary note 17, wherein the feature value stored in the storage unit is defined for each type or material of the target object or the target region.

(Supplementary Note 19)

The computer readable medium according to Supplementary note 15 or 16, wherein the computer includes a model that has been trained to output, in response to an input of data indicating a time variation of a temperature of a region of an object, data indicating the type of wiping work performed on that region, and wherein in the identification of the type of wiping work, the type of wiping work performed on the target region is determined by inputting time-series data included in the acquired temperature data sequence to the model.

(Supplementary Note 20)

The computer readable medium according to Supplementary note 19, wherein the model is provided for each type or material of the target object or the target region, or wherein the data input to the model includes data indicating the type or material of the target object or the target region.

(Supplementary Note 21)

The computer readable medium according to any one of Supplementary notes 15 to 20, wherein in the acquisition of the temperature data sequence, the temperature data sequence is acquired for each of a plurality of the target objects, wherein in the identification of the type of wiping work, for each of the plurality of target objects, the type of wiping work performed on the target region of the target object is determined, and wherein the control method further comprises outputting, together with an image representing the target object, a display enabling a user to know whether or not a specific type of wiping work has been performed on each of the target objects.

This application claims priority on the basis of Japanese Patent Application No. 2021-022854, filed Feb. 16, 2021, the entire disclosure of which is incorporated herein by reference.

REFERENCE SIGNS LIST

10 Target Object
12 Target Region
30 Temperature Sensor
40 Temperature Data Sequence
42 Temperature Data
50 Partial Data Sequence
60 Table
70 State Display
80 State Display
100 Browsing Screen
500 Computer
502 Bus
504 Processor
506 Memory
508 Storage Device
510 Input/Output Interface
512 Network Interface
2000 Work Type Identification Apparatus
2020 Acquisition Unit
2040 Identification Unit

What is claimed is:

1. A work type identification apparatus comprising:

at least one memory that is configured to store instructions; and at least one processor that is configured to execute the instructions to:

acquire, for a target region of a target object on which a wiping work is to be performed, a temperature data sequence that indicates a time variation of a temperature of the target region; and determine a type of wiping work performed on the target region based on the time variation of the temperature of the target region indicated by the temperature data sequence, wherein the type of wiping work includes at least two of a wiping work performed using alcohol, a wet wiping, and a dry wiping.

2. The work type identification apparatus according to claim 1, wherein for each type of wiping work, a feature value of time-series data indicating a time variation of a temperature of a region on which the wiping work of that type is stored in advance in a storage unit, and wherein the determination of the type of wiping work includes: extracting a feature value from time-series data included in the acquired temperature data sequence; and determining the type of wiping work performed on the target region based on a degree of similarity between the extracted feature value and the feature value stored in the storage unit for each type of wiping work.

3. The work type identification apparatus according to claim 2, wherein the feature value stored in the storage unit is defined for each type or material of the target object or the target region.

4. The work type identification apparatus according to claim 1, wherein the at least one memory further stores a model that has been trained to output, in response to an input of data indicating a time variation of a temperature of a region of an object, data indicating the type of wiping work performed on that region, and wherein the determination of the type of wiping work includes: determining the type of wiping work performed on the target region by inputting time-series data included in the acquired temperature data sequence to the model.

5. The work type identification apparatus according to claim 4, wherein the model is provided for each type or material of the target object or the target region, or wherein the data input to the model includes data indicating the type or material of the target object or the target region.

6. The work type identification apparatus according to claim 1, wherein the acquisition of the temperature data sequence includes: acquiring the temperature data sequence for each of a plurality of the target objects, wherein the determination of the type of wiping work includes: determining, for each of the plurality of target objects, the type of wiping work performed on the target region of the target object, and wherein the at least one processor is configured to execute the instructions further to: output, together with an image representing the target object, a display enabling a user to know whether or not a specific type of wiping work has been performed on each of the target objects.

7. A control method executed by a computer comprising:

acquiring, for a target region of a target object on which a wiping work is to be performed, a temperature data sequence that indicates a time variation of a temperature of the target region; and determining a type of wiping work performed on the target region based on the time variation of the temperature of the target region indicated by the temperature data sequence, wherein the type of wiping work includes at least two of a wiping work performed using alcohol, a wet wiping, and a dry wiping.

8. The control method according to claim 7, wherein for each type of wiping work, a feature value of time-series data indicating a time variation of a temperature of a region on which the wiping work of that type is stored in advance in a storage unit, and wherein the determination of the type of wiping work includes: extracting a feature value from time-series data included in the acquired temperature data sequence; and determining the type of wiping work performed on the target region based on a degree of similarity between the extracted feature value and the feature value stored in the storage unit for each type of wiping work.

9. The work type identification apparatus according to claim 8, wherein the feature value stored in the storage unit is defined for each type or material of the target object or the target region.

10. The control method according to claim 7, wherein the computer includes a model that has been trained to output, in response to an input of data indicating a time variation of a temperature of a region of an object, data indicating the type of wiping work performed on that region, and wherein the determination of the type of wiping work includes: determining the type of wiping work performed on the target region by inputting time-series data included in the acquired temperature data sequence to the model.

11. The control method according to claim 10, wherein the model is provided for each type or material of the target object or the target region, or wherein the data input to the model includes data indicating the type or material of the target object or the target region.

12. The control method according to claim 7, wherein the acquisition of the temperature data sequence includes: acquiring the temperature data sequence for each of a plurality of the target objects, wherein the determination of the type of wiping work includes: for each of the plurality of target objects, determining the type of wiping work performed on the target region of the target object, and wherein the control method further comprises outputting, together with an image representing the target object, a display enabling a user to know whether or not a specific type of wiping work has been performed on each of the target objects.

13. A non-transitory computer readable medium storing a program that causes a computer to execute:

acquiring, for a target region of a target object on which a wiping work is to be performed, a temperature data sequence that indicates a time variation of a temperature of the target region; and determining a type of wiping work performed on the target region based on the time variation of the temperature of the target region indicated by the temperature data sequence, wherein the type of wiping work includes at least two of a wiping work performed using alcohol, a wet wiping, and a dry wiping.

14. The computer readable medium according to claim 13, wherein for each type of wiping work, a feature value of time-series data indicating a time variation of a temperature of a region on which the wiping work of that type is stored in advance in a storage unit, and wherein the determination of the type of wiping work includes: extracting a feature value from time-series data included in the acquired temperature data sequence; and determining the type of wiping work performed on the target region based on a degree of similarity between the extracted feature value and the feature value stored in the storage unit for each type of wiping work.

15. The computer readable medium according to claim 14, wherein the feature value stored in the storage unit is defined for each type or material of the target object or the target region.

16. The computer readable medium according to claim 13, wherein the computer includes a model that has been trained to output, in response to an input of data indicating a time variation of a temperature of a region of an object, data indicating the type of wiping work performed on that region, and wherein the determination of the type of wiping work includes: determining the type of wiping work performed on the target region by inputting time-series data included in the acquired temperature data sequence to the model.

17. The computer readable medium according to claim 16, wherein the model is provided for each type or material of the target object or the target region, or wherein the data input to the model includes data indicating the type or material of the target object or the target region.

* * * * *